US00PP35999P2

(12) United States Plant Patent
Matsubara et al.

(10) Patent No.: US PP35,999 P2
(45) Date of Patent: Jul. 9, 2024

(54) ***PETUNIA* PLANT NAMED 'KEIPEMOKOHOS'**

(50) Latin Name: ***Petunia* x *hybrida***
Varietal Denomination: Keipemokohos

(71) Applicant: KEISEI ROSE NURSERIES INC., Chiba (JP)

(72) Inventors: Susumu Matsubara, Chiba (JP); Rieko Suwa, Chiba (JP)

(73) Assignee: KEISEI ROSE NURSERIES INC., Chiba (JP)

( * ) Notice: Subject to any disclaimer, the term of this patent is extended or adjusted under 35 U.S.C. 154(b) by 0 days.

(21) Appl. No.: 18/372,649

(22) Filed: Sep. 25, 2023

(51) Int. Cl.
*A01H 5/02* (2018.01)
*A01H 6/82* (2018.01)

(52) U.S. Cl.
USPC ..... Plt./356.21
CPC ..... *A01H 6/824* (2018.05)

(58) Field of Classification Search
USPC ..... Plt./356.21, 356.22
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Petunia* plant named 'Keipemokohos', characterized by its compact and mounding plant habit; vigorous growth habit; freely branching habit; freely flowering habit; long flowering period; relatively small and deeply-lobed flowers that are purplish pink in color with white-colored throats; and good garden performance.

2 Drawing Sheets

Figure 1:
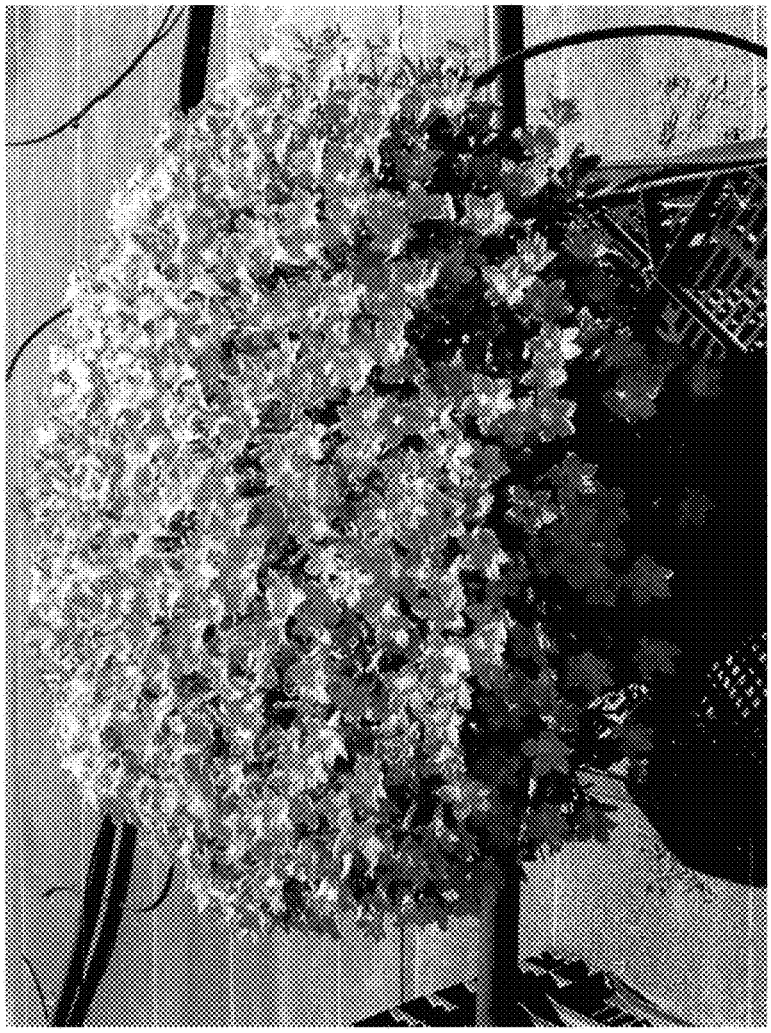

Botanical designation: *Petunia* x *hybrida*.
Cultivar denomination: 'KEIPEMOKOHOS'.

A Japanese Plant Breeder's Rights application for the instant plant was filed by the Applicant/Assignee, Keisei Rose Nurseries Inc. of Yachiyo, Chiba, Japan on Aug. 10, 2023, application number 36977. Foreign priority is not claimed to this application.

BACKGROUND OF THE INVENTION

The present invention relates to a new and distinct cultivar of *Petunia* plant, botanically known as *Petunia* x *hybrida* and hereinafter referred to by the name 'Keipemokohos'.

The new *Petunia* plant is a product of a planned breeding program conducted by the Inventors in Katori, Chiba, Japan. The objective of the breeding program is to create new compact and early-flowering *Petunia* plants with numerous attractive flowers.

The new *Petunia* plant originated from a cross-pollination made by the Inventors in May, 2017 in Katori, Chiba, Japan of an unnamed proprietary selection of *Petunia* x *hybrida*, not patented, as the female, or seed, parent with an unnamed proprietary selection of *Petunia* x *hybrida*, not patented, as the male, or pollen, parent. The new *Petunia* plant was discovered and selected by the Inventors as a single flowering plant within the progeny of the stated cross-pollination in a controlled greenhouse environment in Katori, Chiba, Japan in November, 2017.

Asexual reproduction of the new *Petunia* plant by terminal vegetative cuttings in a controlled greenhouse environment in Katori, Chiba, Japan since November, 2017 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Keipemokohos'. These characteristics in combination distinguish 'Keipemokohos' as a new and distinct *Petunia* plant:

1. Compact and mounding plant habit.
2. Vigorous growth habit.
3. Freely branching habit.
4. Freely flowering habit.
5. Long flowering period.
6. Relatively small and deeply-lobed flowers that are purplish pink in color with white-colored throats.
7. Good garden performance.

Plants of the new *Petunia* can be compared to plants of the female parent selection. Plants of the new *Petunia* differ primarily from plants of the female parent selection in flower color as flowers of plants of the new *Petunia* are purplish pink in color with white-colored throats whereas flowers of plants of the female parent selection are pink in color with brownish-colored venation. In addition, plants of the new *Petunia* are more freely flowering than plants of the female parent selection.

Plants of the new *Petunia* can be compared to plants of the male parent selection. Plants of the new *Petunia* differ primarily from plants of the male parent selection in flower color as flowers of plants of the new *Petunia* are purplish pink in color with white-colored throats whereas flowers of plants of the male parent selection are light pink in color. In addition, plants of the new *Petunia* are more freely flowering than plants of the male parent selection.

Plants of the new *Petunia* can also be compared to plants of the *Petunia* x *hybrida* 'Keipelcumehus', disclosed in U.S.

Plant Pat. No. 35,086. In side-by-side comparisons, plants of the new *Petunia* and 'Keipekumehus' differ primarily in the following characteristics:

1. Plants of the new *Petunia* have shorter internodes than plants of 'Keipekumehus'.
2. Plants of the new *Petunia* have smaller leaves than plants of 'Keipekumehus'.
3. Plants of the new *Petunia* have smaller flowers than plants of 'Keipekumehus'.
4. Plants of the new *Petunia* are more freely flowering than plants of 'Keipekumehus'.
5. Plants of the new *Petunia* and 'Keipekumehus' differ in flower color as flowers of plants of the new *Petunia* are purplish pink in color with white-colored throats whereas flowers of plants of 'Keipekumehus' are reddish purple in color with a white-colored star-shaped pattern and centers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'Keipemokohos' grown in a container.

Figure 2:
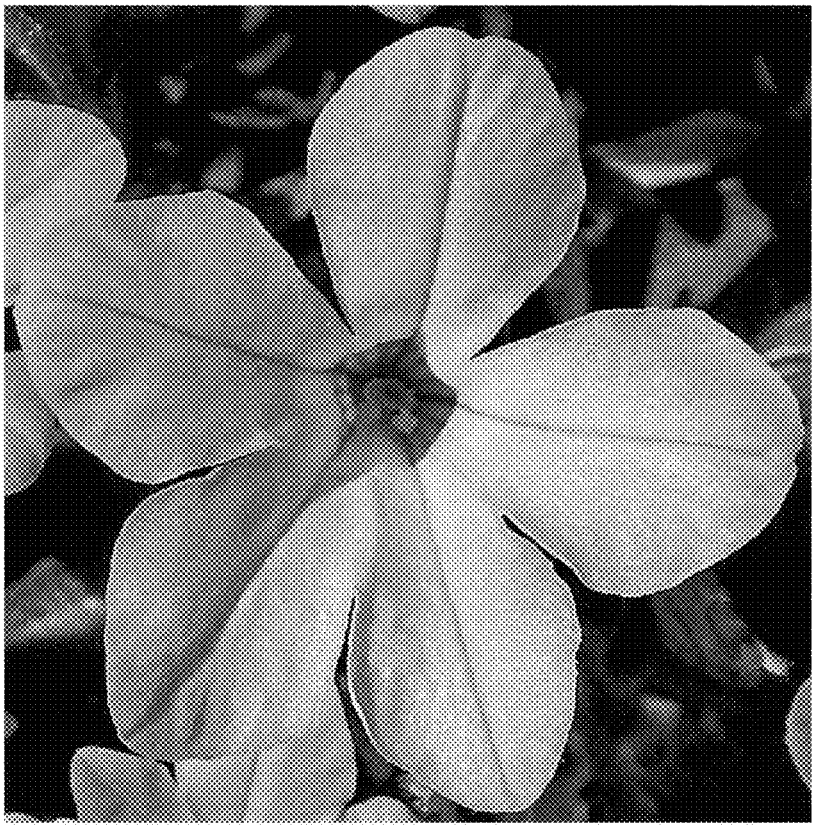

The photograph on the second sheet (FIG. 2) is a close-up view of a typical flower of 'Keipemokohos'.

DETAILED BOTANICAL DESCRIPTION

The aforementioned photographs and following observations, measurements and values describe plants grown during the summer in 24-cm containers in a glass-covered greenhouse in Katori, Chiba, Japan and under cultural practices typical of commercial *Petunia* production. During the production of the plants, day temperatures averaged 35 C and night temperatures averaged 25 C. Plants were pinched one time and were six months old when the photographs and description were taken. In the following description, color references are made to The Royal Horticultural Society Colour Chart, 2007 Edition, except where general terms of ordinary dictionary significance are used.

Botanical classification: *Petunia* x *hybrida* 'Keipemokohos'.

Parentage:

*Female, or seed, parent*.—Unnamed proprietary selection of *Petunia* x *hybrida*, not patented.

*Male, or pollen, parent*.—Unnamed proprietary selection of *Petunia* x *hybrida*, not patented.

Propagation:

*Type*.—By terminal vegetative cuttings.

*Time to initiate roots, summer*.—About one week at temperatures about 25 C.

*Time to initiate roots, winter*.—About three weeks at temperatures about 10 C.

*Time to produce a rooted young plant, summer*.—About three weeks at temperatures about 25 C.

*Time to produce a rooted young plant, winter*.—About four weeks at temperatures about 20 C.

*Root description*.—Medium in thickness, fibrous; typically light brown to white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Compact and mounding plant habit; freely branching habit with numerous lateral branches developing per plant; pinching enhances lateral branch development; vigorous growth habit.

*Plant height*.—About 22 cm.

*Plant diameter*.—About 50 cm.

Lateral branch description:

*Length*.—About 20 cm.

*Diameter*.—About 1.5 mm.

*Internode length*.—About 1 cm.

*Strength*.—Strong, flexible.

*Texture*.—Pubescent.

*Color*.—Close to 144A.

Leaf description:

*Arrangement*.—Alternate, simple.

*Length*.—About 2.7 cm.

*Width*.—About 6 mm.

*Shape*.—Elliptic.

*Apex*.—Narrowly acute.

*Base*.—Attenuate.

*Margin*.—Entire.

*Texture, upper and lower surfaces*.—Pubescent.

*Venation pattern*.—Pinnate.

*Color*.—Developing and fully expanded leaves, upper surface: Close to 138A; venation, close to 147C. Developing and fully expanded leaves, lower surface: Close to 137B; venation, close to 147C.

*Petioles*.—Length: About 6 mm. Diameter: About 1.5 mm. Texture, upper and lower surfaces: Pubescent. Color, upper and lower surfaces: Close to 147C.

Flower description:

*Flower arrangement and habit*.—Single salverform flowers arising from upper leaf axils; freely flowering habit with numerous flowers developing during the flowering season; flowers face upright to outwardly.

*Fragrance*.—Faint; pleasant.

*Natural flowering season*.—Early flowering habit; plants of the new *Petunia* initiate and develop flowers about two to three weeks after planting; long flowering period, plants flower continuously from late March to late October in Japan.

*Flower longevity*.—Individual flowers last about five days on the plant.

*Flower buds*.—Length: About 2.5 cm. Diameter: About 3.5 mm. Shape: Cylindrical. Color: Close to 144C.

*Flower diameter*.—About 2.2 cm.

*Flower depth*.—About 2.5 cm.

*Flower throat diameter*.—About 4 mm.

*Flower tube length*.—About 1.7 cm.

*Flower tube diameter, proximally*.—About 1.5 mm.

*Corolla*.—Quantity and arrangement: Five in a single whorl, fused at the base and opening into a flared trumpet with deep lobes. Petal length from throat: About 1.1 cm. Petal width: About 7 mm. Petal shape: Roughly spatulate. Petal apex: Mucronate. Petal margin: Entire; strongly undulate. Petal texture, upper and lower surfaces: Smooth, glabrous. Throat texture: Smooth, glabrous. Tube texture: Pubescent. Color: Petal, when opening and fully opened, upper surface: Close to 73A; venation, close to 153A; color becoming closer to N74B with subsequent development. Petal, when opening and fully opened, lower surface: Close to N74D; venation, close to 153A; color does not change with subsequent development. Throat: Close to 155C; venation, close to 153A. Tube: Close to NN155B; venation, close to N144B.

*Calyx*.—Arrangement: One star-shaped calyx tube with five sepals arranged in a single whorl and fused at the base. Sepal length: About 7 mm. Sepal width: About 1 mm. Sepal shape: Lanceolate. Sepal apex: Acute. Sepal margin: Entire. Sepal texture, upper and lower surfaces: Pubescent. Color, upper surface: Close to 143A. Color, lower surface: Close to 143C.

*Peduncles*.—Length: About 1.2 cm. Diameter: About 1 mm. Strength: Moderately strong, flexible. Aspect: Upright to outwardly. Texture: Pubescent; viscid. Color: Close to 143A.

*Reproductive organs*.—Stamens: Quantity per flower: Five. Anther shape: Ellipsoidal. Anther size: About 1 mm by 1.5 mm. Anther color: Close to 158D. Pollen amount: Moderate. Pollen color: Close to 155A. Pistils: Quantity per flower: One. Pistil length: About 1.4 cm. Style length: About 1 cm. Style color: Close to 145B. Stigma shape: Roughly round. Stigma color: Close to 143B. Ovary color: Close to 145A. Seeds and fruits: To date, seed and fruit development have not been observed on plants of the new *Petunia*.

Garden performance: Plants of the new *Petunia* have been observed to have good garden performance and to tolerate rain, wind and temperatures ranging from about 5 C to about 35 C.

Pathogen & pest resistance: To date, plants of the new *Petunia* have not been observed to be resistant to pathogens and pests common to *Petunia* plants.

It is claimed:

1. A new and distinct *Petunia* plant named 'Keipemokohos' as illustrated and described.

* * * * *